United States Patent [19]
Schröder et al.

[11] Patent Number: 5,859,084
[45] Date of Patent: Jan. 12, 1999

[54] RADIATION-CURABLE COMPOSITIONS CONTAINING PHOTOINITIATORS LINKED BY A COVALENT BOND

[75] Inventors: Jochen Schröder, Limburgerhof; Wolfgang Reich, Maxdorf; Erich Beck, Ladenburg; Martin Fischer, Ludwigshafen; Wolfram Weiss, Mutterstadt, all of Germany

[73] Assignee: BASF Aktiengesellschaft, Ludwigshafen, Germany

[21] Appl. No.: 679,570

[22] Filed: Jul. 15, 1996

[30] Foreign Application Priority Data

Jul. 22, 1995 [DE] Germany ................. 19526856

[51] Int. Cl.⁶ ................. C08F 2/50; C08F 2/48; C07C 69/96
[52] U.S. Cl. ................. 522/34; 522/35; 522/46; 522/182; 522/90; 522/100; 522/104; 522/905; 558/270; 558/273; 427/510; 427/519; 427/504; 427/506; 430/269
[58] Field of Search ................. 522/46, 34, 35, 522/905, 90, 100, 104; 558/270, 273; 427/510, 519, 504, 506; 430/269

[56] References Cited

U.S. PATENT DOCUMENTS

| | | | |
|---|---|---|---|
| 3,647,881 | 3/1972 | Bays et al. | 260/591 |
| 4,147,604 | 4/1979 | Kuesters et al. | 204/159.23 |
| 4,180,599 | 12/1979 | Wolpert et al. | |
| 4,279,721 | 7/1981 | Kirchmayr et al. | 204/159.24 |
| 4,902,724 | 2/1990 | Moore | 522/40 |
| 5,389,699 | 2/1995 | Rehmer et al. | 522/35 |
| 5,532,112 | 7/1996 | Kohler et al. | 522/33 |
| 5,741,829 | 4/1998 | Reich et al. | 522/35 |

FOREIGN PATENT DOCUMENTS

| | | |
|---|---|---|
| 0 000 342 | 1/1979 | European Pat. Off. . |
| 0 005 530 | 11/1979 | European Pat. Off. . |
| 2001 288 | 7/1970 | Germany . |
| WO 93/21240 | 10/1993 | WIPO . |

*Primary Examiner*—Susan W. Berman
*Attorney, Agent, or Firm*—Oblon, Spivak, McClelland, Maier & Neustadt, P.C.

[57] ABSTRACT

A process for the preparation of a radiation-curable acrylate composition, wherein to compounds A containing at least 2 acrylic groups there are added benzophenone derivatives which are not copolymerizable by free-radical copolymerization and which contain at least one primary or secondary amino group or a hydroxyl group or a mercapto group.

6 Claims, No Drawings

RADIATION-CURABLE COMPOSITIONS CONTAINING PHOTOINITIATORS LINKED BY A COVALENT BOND

The invention relates to a process for the preparation of radiation-curable acrylate compositions.

Radiation-curable acrylates are well known. Usually a photoinitiator is added to radiation-curable acrylates, in order to make it possible to effect curing by irradiation with ultraviolet light. Following irradiation, residues of the photoinitiator may remain in the cured composition as volatile or extractable substances, which is generally undesirable.

Copolymerizable photoinitiators or coreactive photoinitiators are disclosed, eg, by EP-A 281,941. They are predominantly acetophenone derivatives which, as so-called α-splitters, divide into 2 molecules during exposure, of which only one becomes fixed to the polymer via reactive groups.

EP-A 280,222 reveals that the reactivity of radiation-curable compositions based on acrylates can be increased by the addition of primary or secondary amines. The primary or secondary amines undergo a Michael-like addition at the acrylic double bond.

The object of the present invention is to provide radiation-curable acrylates and compositions possessing high radiation-induced curing reactivity and containing small amounts of volatile or extractable substances.

Accordingly, we have found a process for the preparation of radiation-curable acrylate compositions, wherein to compounds A containing at least 2 acrylic groups there are added benzophenone derivatives which are not copolymerizable by free-radical copolymerization and which contain at least one primary or secondary amino group or a hydroxyl group or a mercapto group. We have also found the radiation-curable compositions produced by said process. We have also found benzophenone derivatives suitable for the above process.

The following statements relate to preferred embodiments of the invention.

The essential components of the process for the preparation of radiation-curable compositions are compounds A containing at least two acrylic groups. The primary or secondary amino group or the hydroxyl group or mercapto group of the benzophenone derivatives can add to the acrylic group in the manner of a Michael-like addition

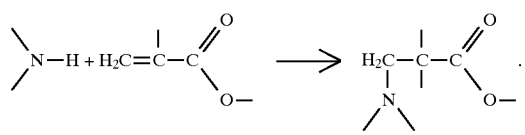

Primary amino groups then become secondary amino groups, and secondary amino groups become tertiary amino groups.

By compounds A are meant not only derivatives of acrylic acid but also derivatives of methacrylic acid. However, the derivatives of acrylic acid are preferred.

The compounds A contain on the average preferably from 2 to 20, more preferably from 2 to 10 and most preferably from 2 to 6 acrylic groups in the molecule.

The number-average molecular weight $M_n$ of the compounds A is preferably below 15000, more preferably below 5000 and most preferably below 3000 g/mol (as determined by gel permeation chromatography using polystyrene as standard and tetrahydrofuran as eluant).

Examples of compounds A are acrylates of polyfunctional alcohols, particularly those containing, apart from the hydroxyl groups, no other functional groups except for, at most, ether groups. Examples of such alcohols are bifunctional alcohols such as ethylene glycol, propylene glycol, and higher condensation products thereof, eg, diethylene glycol, triethylene glycol, dipropylene glycol, tripropylene glycol, etc., butane diol, pentane diol, hexane diol, neopentyl glycol, alkoxylated phenolic compounds such as ethoxylated or propoxylated bisphenol, cyclohexane dimethanol, trifunctional alcohols and alcohols of higher functionality, such as glycerol, trimethylol propane, butane triol, trimethylol ethane, pentaerythritol, ditrimethylol propane, dipentaerythritol, sorbitol, mannitol, and the corresponding alkoxylated, particularly ethoxylated and propoxylated, alcohols.

The alkoxylation products can be obtained in known manner by the reaction of the above alcohols with alkylene oxides, particularly ethylene or propylene oxide. Preferably the degree of alkoxylation of each hydroxyl group is from 0 to 10, ie 1 mol of hydroxyl group can preferably be alkoxylated with up to 10 mol of alkylene oxide.

Further examples of suitable acrylate compounds are polyester acrylates, these being the acrylates of polyesterols.

Examples of suitable polyesterols are those such as can be prepared by esterification of polycarboxylic acids, preferably dicarboxylic acids, with polyols, preferably diol. The starting materials for such hydroxyl group-containing polyesters are known to the person skilled in the art. Dicarboxylic acids that may be used are preferably succinic acid, glutaric acid, adipic acid, sebacic acid, o-phthalic acid, their isomers and hydrogenation products and also esterifiable derivatives, such as anhydrides or dialkylesters of said acids. Suitable polyols are the alcohols specified above, preferably ethylene glycol, 1,2-propylene glycol, 1,3-propylene glycol, 1,4-butane diol, 1,6-hexane diol, neopentyl glycol, cyclohexane dimethanol and also polyglycols of ethylene glycol and propylene glycol types.

Polyester acrylates may be prepared in several stages or alternatively in a single stage, as described, for example, in EP 279,303, from acrylic acid, polycarboxylic acid, and polyol.

Compounds A, may also be, eg, epoxide or urethane acrylates.

Epoxide (meth)acrylates are, eg, those such as can be prepared by the reaction of epoxidized olefins or polyethers or diglycidyl ethers, such as bisphenol-A diglycidyl ether, with (meth)acrylic acid.

The reaction is known to the person skilled in the art and is described, eg, in R. Holmann, U. V. And E. B. Curing Formulation for Printing Ink and Paint, London 1984.

Urethane acrylates are, in particular, reaction products of hydroxyalkyl acrylates with polyisocyanates or diisocyanates (cf R. Holmann, U. V. And E. B. Curing Formulation for Printing Ink and Paint, London 1984).

Of course, mixtures of different compounds A may be used if desired.

The benzophenone derivatives are added to the compounds A of the invention. In this case a Michael addition takes place without any necessity to increase the temperature. The use of higher temperatures can accelerate the Michael addition. The temperature is generally kept at from 0° to 200° C., preferably 15° to 80° C.

The benzophenone derivatives are photoinitiators for the free radical polymerization.

The benzophenone derivatives preferably contain a primary or secondary amino group.

In particular, the benzophenone derivatives are those of the formula

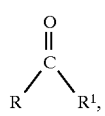

I in which R stands for a phenyl radical or for $R^1$ and $R^1$ stands for the radical

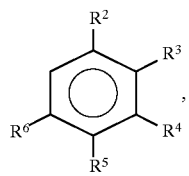

where the radicals $R^2$ to $R^6$ independently denote H, a $C_1$–$C_4$ alkyl or $C_1$–$C_4$ alkoxy group, and at least one, but not more than three, of the radicals $R^3$ bis $R^6$ stands for a group X, and X denotes an organic group containing from 1 to 30 C atoms and containing a primary amino group, a secondary amino group, or a hydroxyl or mercapto group.

Each of the radicals $R^2$ to $R^6$, when not denoting a group X, is preferably a hydrogen atom.

In particular, only one of the radicals $R^2$ to $R^6$ stands for a group X and preferably $R^4$ stands for a group X.

X is, eg, an aromatic or, in particular, an aliphatic group containing from 1 to 20 and more preferably from 1 to 10 C atoms and containing a hydroxyl group, and preferably containing a primary or secondary amino group.

R preferably stands for a phenyl radical.

The following compounds are given as examples of the benzophenone derivatives of the invention:

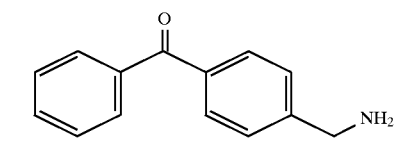

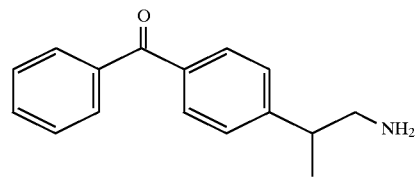

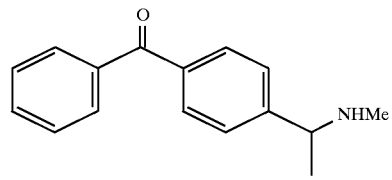

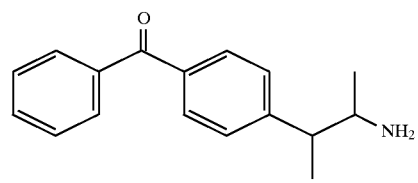

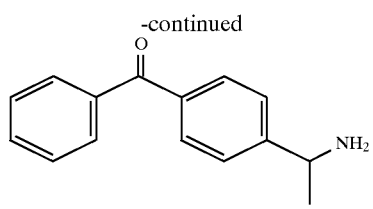

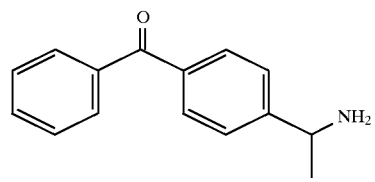

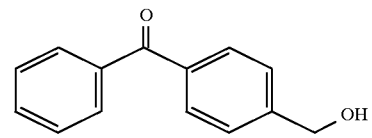

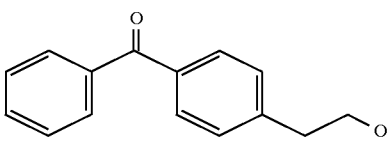

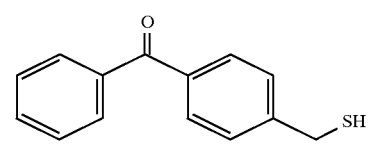

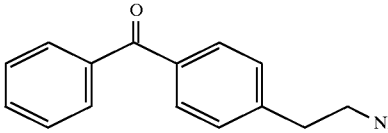

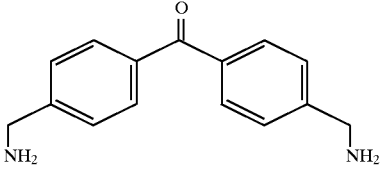

Different processes I to III are available for the preparation of the benzophenone derivatives of the invention.

Process I

This processes is characterized in that a compound of the formula I, in which however at least one, but not more than three, of the radicals $R^3$ to $R^6$ is a $C_1$–$C_{20}$ alkyl radical instead of a group X, is used as starting material, the alkyl radical is chlorinated with elementary chlorine and then caused to react with sodium diformylamide and hydrolyzed.

Chlorination with elementary chlorine is preferably carried out at temperatures ranging from 0° to 100° C., so that only the alkyl radical is chlorinated.

The product obtained is then caused to react with a sodium diformylamide preferably at temperatures ranging from 0° to 100° C., during which substitution of the chlorine by a formylamino group takes place:

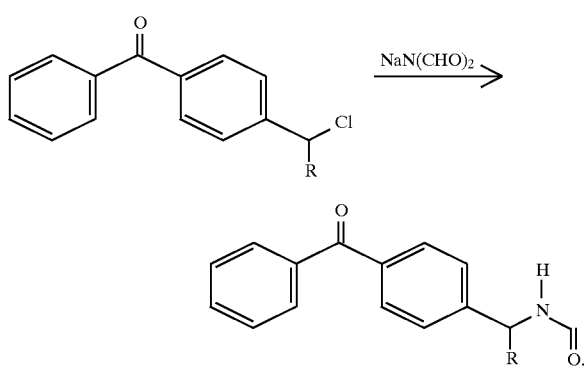

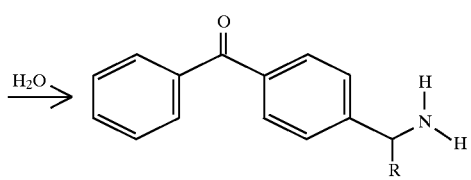

Subsequent hydrolysis with water then provides the desired end product:

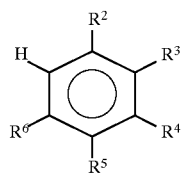

Process II
This process is characterized in that
a benzotrichloride derivative is caused to react with an aromatic compound of the formula

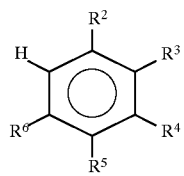

to form a benzophenone derivative in which the variables have the meanings specified above except that at least one, but not more than three, of the radicals $R^3$ to $R^6$ stands for an organic radical containing a tertiary amino group masked with a protective group instead of for X and
the protective group is eliminated by acid hydrolysis.

The reaction producing the benzophenone derivative is preferably carried out at temperatures ranging from −20° to 20° C. and in the presence of a catalyst, eg, aluminum chloride or a zeolite. The protective group on the tertiary amine is preferably an acetyl radical.

Finally, the protective group can be eliminated in known manner, eg, by acid hydrolysis, in which case a primary or secondary amine is obtained in the side chain.

Process III
This process is characterized in that
an aromatic compound of the formula

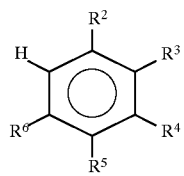

in which the variables have the meanings specified above except that at least one, but not more than three, of the radicals $R^3$ to $R^6$ stands for an organic radical containing a carbonyl group instead of for X, is condensed with an aliphatic nitro compound, the compound obtained is caused to react with a benzotrichloride derivative to produce a benzophenone derivative, and the nitro group is subsequently hydrogenated.

In this process an aromatic carbonyl compound is first of all condensed with a nitro compound, preferably an aliphatic nitro compound according to the scheme:

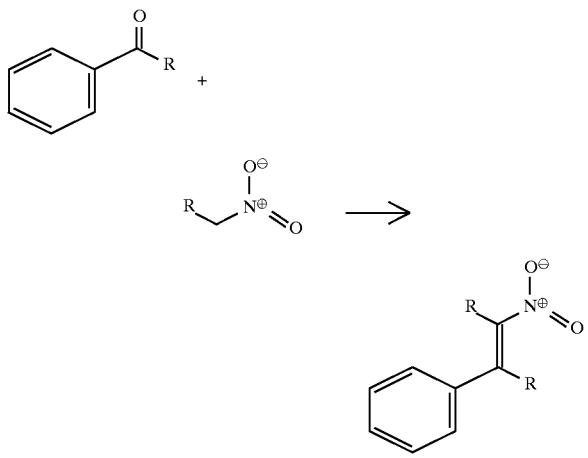

preferably at temperatures ranging from 50° to 150° C.

The double bond is subsequently hydrogenated with hydrogen:

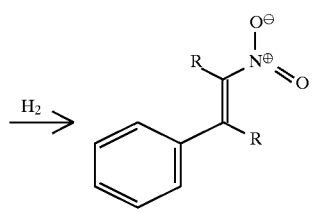

And the product, as under II above, is caused to react with a trichlorobenzene derivative according to the scheme:

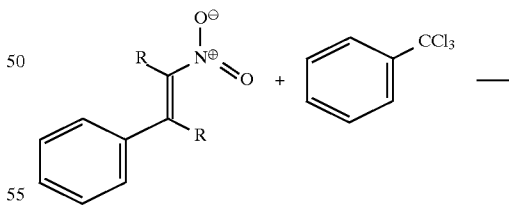

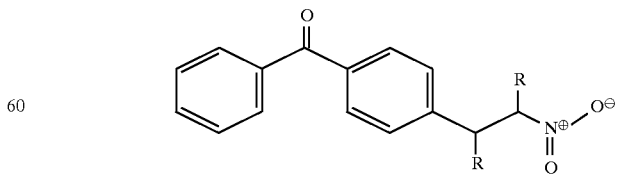

The nitro group in the resulting benzophenone derivative is subsequently hydrogenated with hydrogen to form the amino group:

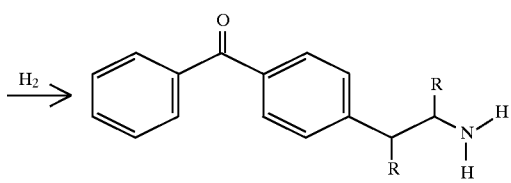

The addition of the benzophenone derivatives to the compounds A produces radiation-curable acrylate compositions containing photoinitiators linked by a covalent bond (by Michael addition). The amount of the benzophenone derivatives should be calculated such that preferably not more than 70 mol %, more preferably not more than 50 mol % and most preferably not more than 30 mol % of the acrylic groups in the compounds A exist as Michael adducts with the benzophenone derivative, so that a sufficient number of double bonds is still present for free radical polymerization.

Generally, however, the amount should be calculated such that at least 0.1 mol %. preferably at least 0.5 mol % of the acrylic groups exist as Michael adducts with the benzophenone derivative.

Of course, the radiation-curable acrylate compositions of the invention may be used as radiation-curable compositions in admixture with other compounds capable of undergoing free radical polymerization.

Preferably the radiation-curable compositions contain from 1 to 100 wt %, more preferably from 20 to 100 wt % and most preferably from 50 to 100 wt % of the radiation-curable acrylate composition A of the invention, based on the total amount of compounds capable of undergoing free radical copolymerization.

Examples of other suitable compounds capable of undergoing free radical polymerization are monoacrylates, eg, $C_1$–$C_{10}$ alkyl (meth)acrylates, vinyl aromatics, eg, styrene, vinyl esters, eg, vinyl acetate, vinyl halides, vinyl nitrites, also copolymerizable oligomers or polymeric compounds.

The other compounds capable of undergoing free radical polymerization may have already been added to compounds A prior to the addition of the benzophenone derivatives.

Preferably the other compounds capable of undergoing free radical polymerization are added following the addition of the benzophenone derivatives, We after the radiation-curable acrylate compositions of the invention have been made.

The content of the benzophenone derivatives in the radiation-curable compositions is preferably from 0.1 to 10 wt %, based on the total amount of the compounds capable of undergoing free radical polymerization. A content of from 0.5 to 5wt % is more preferred (the weight of the benzophenone derivative being calculated as added, ie in unattached form).

The radiation-curable compositions or acrylate compositions of the invention are suitable, eg, for use as coating compositions such as varnishes or printing inks or for the preparation of shaped articles, for the preparation of photoresists, in stereolithography or as molding compositions, eg, for optical lenses.

The compositions or acrylate formulations may contain further additives as conventionally used for said applications.

In the preferred use as coating compositions examples of said additives are thickeners, levelling agents, fillers or pigments.

The compositions or acrylate formulations are preferably cured by irradiation with ultraviolet light and exhibit high reactivity in this respect. The coatings or other products obtained have good mechanical properties, a high degree of hardness and scarcely contain volatile or extractable photoinitiators or benzophenone components.

EXAMPLES

Preparation of Benzophenone Derivatives

A) 4-aminomethylbenzophenone (process I)

i) 4-(chloromethyl)benzophenone 196.2 g of 4-methylbenzophenone are dissolved in chlorobenzene and then gassed at 80° C. in the presence of 1.6 g of AIBN (azodiisobutyronitrile) with a total of 71.0 g of chlorine. The reaction mixture is concentrated and the solid material obtained recrystallized from 1 L of ethanol.

Yield: 150 g

U.V.: $\lambda_{max}$=343 nm, $\epsilon$=173.9 (in toluene).

ii) 4-(N-formylaminomethyl)benzophenone 150 g of formamide are stirred together with 90 mL of 30%ig sodium methylate solution for 8 hours under slight vacuum at 80° C. To the resulting solution of sodium diformylamide there are added 150 g of 4-chloromethylbenzophenone. After 15 hours the suspension originally present has changed to a clear solution which is added to 1l of 10%ig sodium carbonate solution. A solid material precipitates, which is filtered off in vacuo and dried.

Yield: 126 g

U.V.: $\lambda_{max}$=344 nm, $\epsilon$=150.5 (in toluene).

iii) 4-aminomethylbenzophenone 70 g of 4-(N-formylaminomethyl)benzophenone are stirred in a mixture of 40 g of concentrated hydrochloric acid and 100 g of ethanol for 5 hours at 50° C. The alcohol is then removed by distillation and the pH is adjusted to 10 with sodium hydroxide solution. 4-aminomethylbenzophenone precipitates as an oil.

Yield: 20 g

U.V.: $\lambda_{max}$=343 nm, $\epsilon$=155.8 (in toluene).

B) 4-(N-methylaminomethyl)benzophenone (process II)

4-(N-acetyl-N-methylam inomethyl )benzophenone 40 g of $AlCl_3$ are dissolved in 100 mL of dichloroethane and 21.5 g of benzotrichloride are added at a temperature ranging from 0° to 5° C. There are then added 16.3 g of N-methylbenzylacetamide as a solution in dichloroethane (temperature 0° to 50° C.). On completion of the generation of HCl the batch is added to 500 g of ice-water and then hydrolyzed at 70° C. From the organic phase there are isolated 30 g of solid material which is used as such in the next stage.

Alternatively, the following procedure may be used:

21.5 g of benzotrichloride and 16.3 g of N-methylbenzylacetamide are dissolved in 100 mL of dichloroethane and mixed with 1 g of HZSM-5 ($SiO_2$/$Al_2O_3$=40:1) and the mixture is boiled under reflux until the generation of HCl stops. There are then added 500 mL of ice-water and the mixture is hydrolyzed at 70° C. From the organic phase there are isolated 30 g of solid material which is used as such in the next stage.

4-(N-methylam inomethyl )benzophenone 22 g of 4-(N-acetyl-N-methylaminomethyl) benzophenone are refluxed in 100 mL of 1:1 -HCl/water mixture (by volume) for 7 hours. From the reaction mixture there are isolated 16 g of 4-(N-methylaminomethyl) benzophenone. HNMR: $\delta$=1.7 (1H, NH), 2.5 (3H, $NCH_3$), 3.9 (2H, $NCH_2$), 7.1–7.4 (9H, aromatics).

C) 4-(2-aminoethyl)benzophenone 4-(2-N-acetylaminoethyl)benzophenone 40 g of $AlCl_3$ are dissolved in 100 mL of dichloroethane and 21.5 g of benzotrichloride are added at a temperature ranging from 0° to 5° C. There are then added 16 g of N-phenylethylacetamide as a solution in dichloroethane (temperature 0° to 5° C.). On completion of the generation of HCl the batch is added to 500 g of ice-water and then hydrolyzed at 70° C. From the organic phase there are isolated 30 g of solid material which is used as such in the next stage.

Alternatively, the following procedure may be used:

21.5 g of benzotrichloride and 16 g of N-phenylethylacetamide are dissolved in 100 mL of dichloroethane and mixed with 1 g of HZSM-5 ($SiO_2/Al_2O_3$=40:1) and the mixture is boiled under reflux until the generation of HCl stops. There are then added 500 mL of ice-water and the mixture is hydrolyzed at 70° C. From the organic phase there are isolated 30 g of solid material which is used as such in the next stage.

4-(N-am inoethyl )benzophenone 22 g of 4-(2-N-acetyl-aminomethyl)benzophenone are refluxed in 100 mL of 1:1-HCl/water mixture (by volume) for 7 hours. From the reaction mixture there are isolated 16 g of 4-(2-aminoethyl)benzophenone.

HNMR: δ=1.3 (2H, NH), 2.9 and 3.1 (each 2H, $NCH_3$), 7.1–7.4 (9H, aromatics))

Tests a) Reactivity

The photoinitiators were formulated with acrylic ester resins in the proportions (by weight) listed in the table below. The tests were carried out after the formulations had stood for 24 hours. The viscosities were determined using a cone-and-plate viscometer. The cure speed under U.V. Radiation was measured by passing films of varnish, created on art paper using a 15 mm spiral applicator, on a conveyor belt at a distance of 10 cm below an undoped high-pressure mercury irradiator (sold by IST, type: CK1). The belt speed and number of irradiation cycles are a measure of the irradiated light intensity which is required to achieve a tack-free and non-marring coating.

The faster the belt speed and the fewer the irradiation cycles required to give tack-free and non-marring coatings, the higher is the reactivity.

| Varnish | Photoinitiator | Parts ** | Resin Laromer ® 100 parts | Belt Speed Viscosity | Number of m/min | Irradiation Cycles |
|---|---|---|---|---|---|---|
| 1 | A | 3.3 | P083F[1] | 110 | 10 | 2 |
| 2 | B | 3 | P033F[2] | 120 | 10 | 2 |
| 3 | B | 3 | P083F | 130 | 10 | 1 |
| 4 | B | 3.71 | P033F | 95 | 20 | 1 |
| 5 | C | 3 | P033F | 95 | 10 | 6 |
| 6 | C | 3 | P083F | 100 | 10 | 2 |
| 7 | B | 5 | LR8765[3] | 900 | 10 | 1 |
| 8 | B | 5 | LR8799[4] | 4600 | 10 | 1 |
| 9 | B | 5 | LR8945X[5] | 650 | 15 | 1 |
| 10* | benzophenone | 2.4 | PO 83 F | 100 | 15 | 1 |

Laromer ® registered trade mark of BASF AG
*comparative example including an additional 1.6 parts of methyldiethanolamine as coinitiator
**parts by weight based on Laromer, where in Exampies 1, 3, and 10 identical molar amounts of photoinitiator and in Examples 1 and 10 identical molar amounts of amine were present.
[1] an amine-modified polyetheracrylate
[2] a polyetheracrylate
[3] an aliphatic epoxide acrylate
[4] a polyester acrylate
[5] a polyether acrylate b) Extraction Film Preparation Films were produced on glass plates with the varnishes 7 to 10 using a 200 mm spiral applicator and exposed 5 times at 10 m/min. The solid films of varnish were peeled off the glass for extraction.

Extraction

Into a U.V.-opaque brown glass bottle there were poured 25 g of methylene chloride. To this there was added a weighed amount of crushed solid varnish (4 g) and hexadecane as internal standard (0.2 g). The mixture was stirred for 48 h and subsequently analyzed by gas chromatography for residual photoinitiator.

Residues of the photoinitiators of the invention could not be found above the detection limit of 0.1% based on the amount of varnish used. In the comparative example using benzophenone as initiator 80% were found however. The same results were obtained after storage of the films of varnish in the dark over a period of one week.

We claim:

1. A process for preparation of a radiation-curable acrylate compound, comprising reacting a compound A containing at least 2 acrylic groups with a benzophenone derivative wherein said benzophenone is not copolymerizable by free-radical copolymerization and wherein said benzophenone comprises at least one primary or secondary amino group; wherein said benzophenone derivative reacts with said compound A by Michael addition to an acrylic group of said compound A; wherein no more than 50 mol % of the acrylic groups in said compound A exist as Michael adducts with said benzophenone:

wherein said benzophenone derivative is one of the formula:

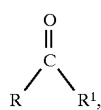

in which R is a phenyl radical or $R^1$, and $R^1$ is a radical:

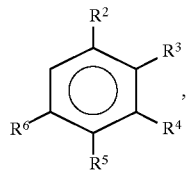

where the radicals $R^2$ to $R^6$ independently denote H, a $C_1$–$C_4$ alkyl or $C_1$–$C_4$ alkoxy group, and at least one, but not more than three, of the radicals $R^3$ to $R^6$ is a group X, and X is $C_1$–$C_{30}$ aliphatic or aromatic group containing a primary amino group or a secondary amino group.

2. The process of claim 1, wherein $R^2$, $R^3$, $R^5$, and $R^6$ each is a hydrogen atom and $R^4$ is X.

3. The process of claim 1, wherein X is a $C_1$–$C_{20}$ aliphatic group containing a primary or secondary amino group.

4. A radiation-curable acrylate compound obtained by the process of claim 1.

5. A process as defined in claim 1, wherein the benzophenone derivative is 4-aminomethylbenzophenone.

6. A method of applying a radiation-curable acrylate compound as defined in claim 4 to a substrate and curing the compound by exposure to radiation.

* * * * *